US007127038B2

United States Patent
(12) United States Patent
Kondradsson et al.

(10) Patent No.: US 7,127,038 B2
(45) Date of Patent: Oct. 24, 2006

(54) X-RAY GRID ARRANGEMENT

(75) Inventors: Dick Kondradsson, Växjö (SE); Lennart Rapp, Malmö (SE); Jonas Ernfridsson, Stockholm (SE)

(73) Assignees: Arcoma AB, Växjö (SE); Gridline AB, Stockholm (SE)

(*) Notice: Subject to any disclaimer, the term of this patent is extended or adjusted under 35 U.S.C. 154(b) by 82 days.

(21) Appl. No.: 10/512,774

(22) PCT Filed: Apr. 17, 2003

(86) PCT No.: PCT/SE03/00624

§ 371 (c)(1), (2), (4) Date: Dec. 4, 2004

(87) PCT Pub. No.: WO03/092503

PCT Pub. Date: Nov. 13, 2003

(65) Prior Publication Data

US 2005/0175154 A1 Aug. 11, 2005

(30) Foreign Application Priority Data

Apr. 30, 2002 (SE) .................................... 0201295

(51) Int. Cl.
*G21K 1/00* (2006.01)

(52) U.S. Cl. ....................................... 378/155; 378/154

(58) Field of Classification Search ................ 378/154, 378/155

See application file for complete search history.

(56) References Cited

U.S. PATENT DOCUMENTS 1,948,270 A 2/1934 Liberson
4,597,096 A 6/1986 Larsson
4,780,904 A * 10/1988 Winter ........................ 378/154
5,291,539 A 3/1994 Thumann et al.
5,357,553 A 10/1994 Ferlic et al.

FOREIGN PATENT DOCUMENTS

| DE | 43 05 475 | 9/1994 |
|---|---|---|
| DE | 197 29 596 | 1/1999 |
| JP | 2000217813 | 1/2001 |
| WO | WO 01/39210 | 5/2001 |

* cited by examiner

*Primary Examiner*—Edward J. Glick
*Assistant Examiner*—Jurié Yun
(74) *Attorney, Agent, or Firm*—Buchanan, Ingersoll & Rooney PC

(57) ABSTRACT

The invention relates to a grid holder for an X-ray diagnostic system. The grid holder cooperates with a flexible X-ray grid, which in a flat state has a first focus distance/convergence distance of about 120 cm. A flexing means, preferably in the form of an inflatable element, which can exert a pressure on the surface of the grid, is arranged to flex the grid in a first direction to a first position in which it has a second convergence distance of about 180 cm. Another corresponding flexing means is arranged to flex the grid in the opposite direction to a second position in which it has a third convergence distance of about 80 cm. This allows variable convergence distances with minimum flexing of the grid. The invention also relates to grid devices with grid holders and grids as well as X-ray diagnostic systems comprising such grid holders/grid devices.

20 Claims, 3 Drawing Sheets

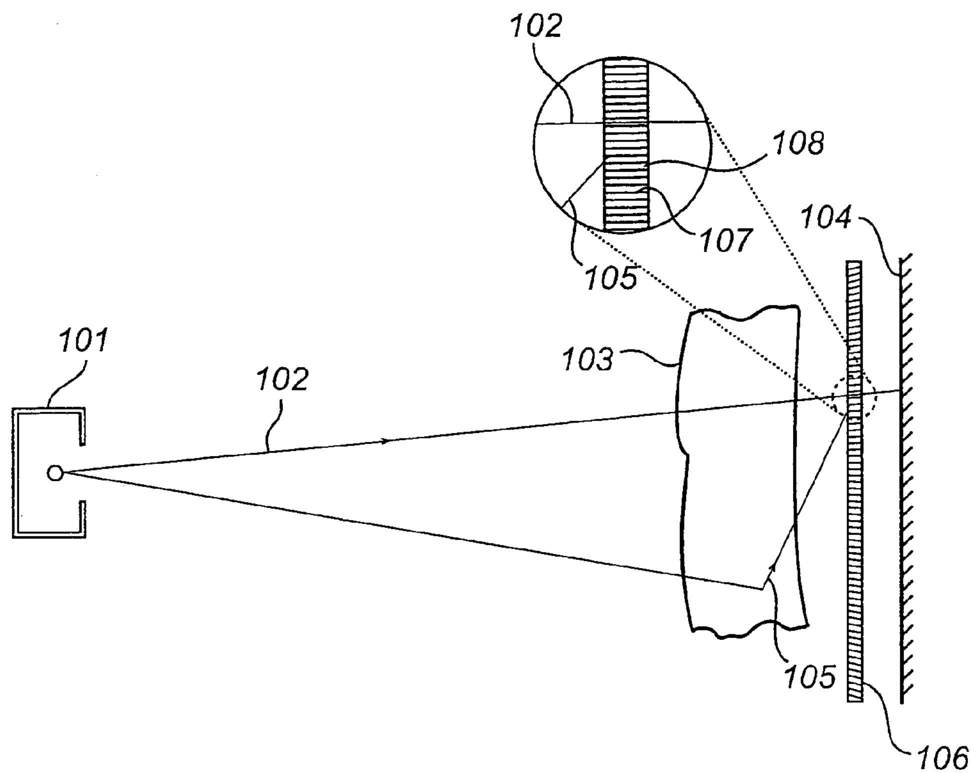
(PRIOR ART) *Fig. 1*
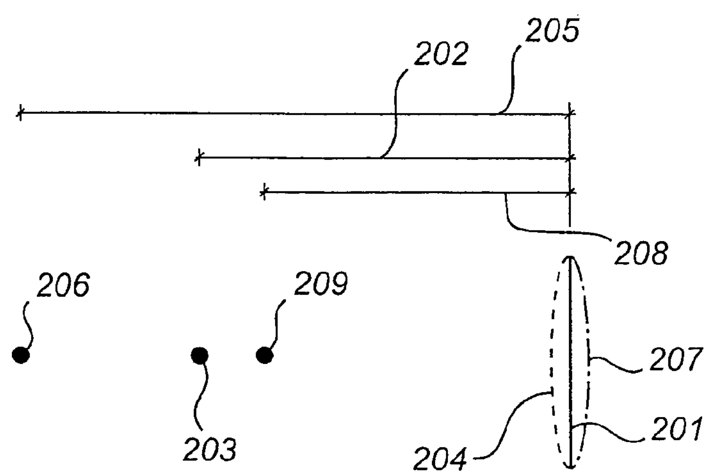
*Fig. 2*

X-RAY GRID ARRANGEMENT

FIELD OF THE INVENTION

The present invention relates to a grid holding device for a medical X-ray diagnostic system according to the preamble to claim 1, a grid device according to the preamble to claim 8, and X-ray diagnostic systems according to the preamble to claims 10 and 11, respectively.

BACKGROUND ART

X-ray grids are used in X-ray diagnostic systems to reduce the noise occurring in a radiograph due to secondary radiation. An X-ray grid comprises a large number of slats of lead, which allow most of the primary radiation generated by an X-ray source to pass and which absorb most of the secondary radiation generated in an irradiated object. The grid is placed between the X-rayed object and the X-ray plate/film which is to be exposed.

To function satisfactorily, the slats of an X-ray grid are often oriented such that their planes converge in a line located at a predetermined distance from the X-ray grid. This distance may be referred to as the convergence distance (or FFD=Film Focus Distance). If an X-ray source is placed in the above-mentioned line, the X-ray grid functions optimally, i.e. a maximum portion of the primary radiation is transmitted and a maximum portion of the secondary radiation is absorbed.

It is desirable, however, to be able to use several different convergence distances in one and the same X-ray diagnostic system. For example, 80 cm may be a suitable distance for X-raying a patient's skull, 120 cm may be a suitable distance for X-ray diagnostics of internal organs of a patient in a horizontal position, and 180 cm may be suitable when X-raying the lungs of a patient in an upright position. An X-ray diagnostic system which is to be applicable to all three distances mentioned above may thus need three separate and replaceable grids to function optimally. Since the cost of an X-ray grid is very high, the system will be expensive to manufacture. Therefore, it has been suggested to use grids with variable convergence distances.

U.S. Pat. No. 5,291,539 discloses a variable grid system in which two opposite edges of a grid structure are each fixed in a rotatable holder. In the flat state, the grid has a convergence distance of about 180 cm. By flexing the grid, this distance can be reduced.

One drawback of such a technique is that a significant reduction of the convergence distance from 180 cm to, for example, 80 cm requires considerable flexing of the grid. Considerable flexing may result in the curvature of the grid not necessarily describing the circumferential surface of a circular cylinder, which means that the convergence distance will not be unambiguous, i.e. the planes of the slats will not coincide in a distinct line.

If a grid is fixed in rotatable holders in this manner, it is also difficult or in any case time-consuming to remove the grid so that an exposure can be made without a grid. This is preferable in X-ray diagnostics of children, on the one hand, because in this case extra low radiation doses are desirable (elimination of the X-ray grid allows the radiation dose to be reduced to a third) and, on the other hand, because a child's skeleton generates relatively little secondary radiation.

DE-C1-43 05 475 discloses another example of a grid system. In this document, use is made of a grid which in the flat state has parallel slats. Different flexed states of the grid are obtained by two opposite edges being loaded to a variable degree towards each other or by the grid being fixed over a vacuum chamber with variable pressure. This system also requires considerable flexing of the grid to obtain a short convergence distance. Also in this case, the grid has to be firmly fixed in its grid holder.

SUMMARY OF THE INVENTION

One object of the present invention is to completely or partly eliminate the above-mentioned drawbacks.

This object is achieved by means of a grid holding device for a medical X-ray diagnostic system according to claim 1, a grid device according to claim 8, and an X-ray diagnostic system according to claim 10 or 11.

According to a first aspect, the invention, more specifically, relates to a grid holding device for a medical X-ray diagnostic system, which device is adapted to cooperate with a flexible, plate-shaped X-ray grid, which in a flat state has a first convergence distance, and which device comprises a flexing means for flexing the X-ray grid in order to adjust the convergence distance of the X-ray grid. The grid holding device is characterised in that the flexing means comprises a first means for flexing the X-ray grid in a first direction, from the flat state to a first predetermined flexed position in which the grid has a second convergence distance, which is longer than the first convergence distance, and a second means for flexing the X-ray grid in a second direction from the flat state to a second predetermined flexed position, in which the grid has a third convergence distance, which is shorter than the first convergence distance. With such a device, a great difference can be obtained between the shortest and the longest convergence distance, without considerable flexing of the grid being required. Instead, the grid is bent or flexed to a lesser extent, but in two different directions. Furthermore, the grid holder can be made compact.

In a preferred embodiment, the first means for flexing comprises a first inflatable element with an elastic wall, which is arranged to exert a pressure, when the element is inflated, on one flat surface of the X-ray grid. When using such a holding device, a grid can easily be inserted and removed, since it does not have to be fixed by screws in the flexing means. Preferably, also the second flexing means comprises a corresponding, inflatable element, which acts on the other surface of the grid.

The walls of these elements are preferably arranged to exert a pressure on the X-ray grid in an area, which is located about a centre line between two opposite edges of the grid, which yields an advantageous curvature of the grid.

In a preferred embodiment, the grid holding device further comprises a box with a lid and a bottom, which are both X-ray transparent. The box is arranged to contain the X-ray grid and the first and the second flexing means. This results in a compact holding device which is easy to handle.

Preferably, the grid holding device comprises at least a first and a second pair of resilient beads. The first bead in each pair is attached to the underside of the lid and the second bead in each pair is attached to the bottom of the box, opposite the first bead in the respective pairs. The pairs of beads can be arranged to fix the X-ray grid in the box. Using such a grid holding device, the grid can easily be removed when an exposure without a grid is desired.

In one embodiment, the pressure can be variable in some of the beads. The beads on one side of the grid can then contribute to the curvature of the grid by loading the edges of the grid in the direction opposite to the direction in which the centre line of the grid is loaded by the inflatable elements on the opposite side. This allows an even more compact design of the grid box.

According to a second aspect, the invention relates to a grid device, comprising a flexible, plate-shaped X-ray grid, which in a flat state has a first convergence distance, and a grid holding device as described above. Such a grid device gives the same advantages as the grid holding device.

The first convergence distance of the grid device can preferably be in the range of 110–130 cm, the second convergence distance in the range of 170–190 cm and the third convergence distance in the range of 70–90 cm.

According to a third aspect, the invention relates to an X-ray diagnostic system, which comprises a grid holding device as described above.

According to a fourth aspect, the invention relates to an X-ray diagnostic system, which comprises a grid device as described above.

The X-ray diagnostic systems according to the third and fourth aspects of the invention give the same advantages as the grid holding device and the grid device according to the invention.

BRIEF DESCRIPTION OF THE DRAWINGS

FIG. 1 schematically shows an X-ray system according to prior-art technique.

FIG. 2 schematically shows the function of a grid device according to an embodiment of the invention.

DESCRIPTION OF PREFERRED EMBODIMENTS

Figure 3:
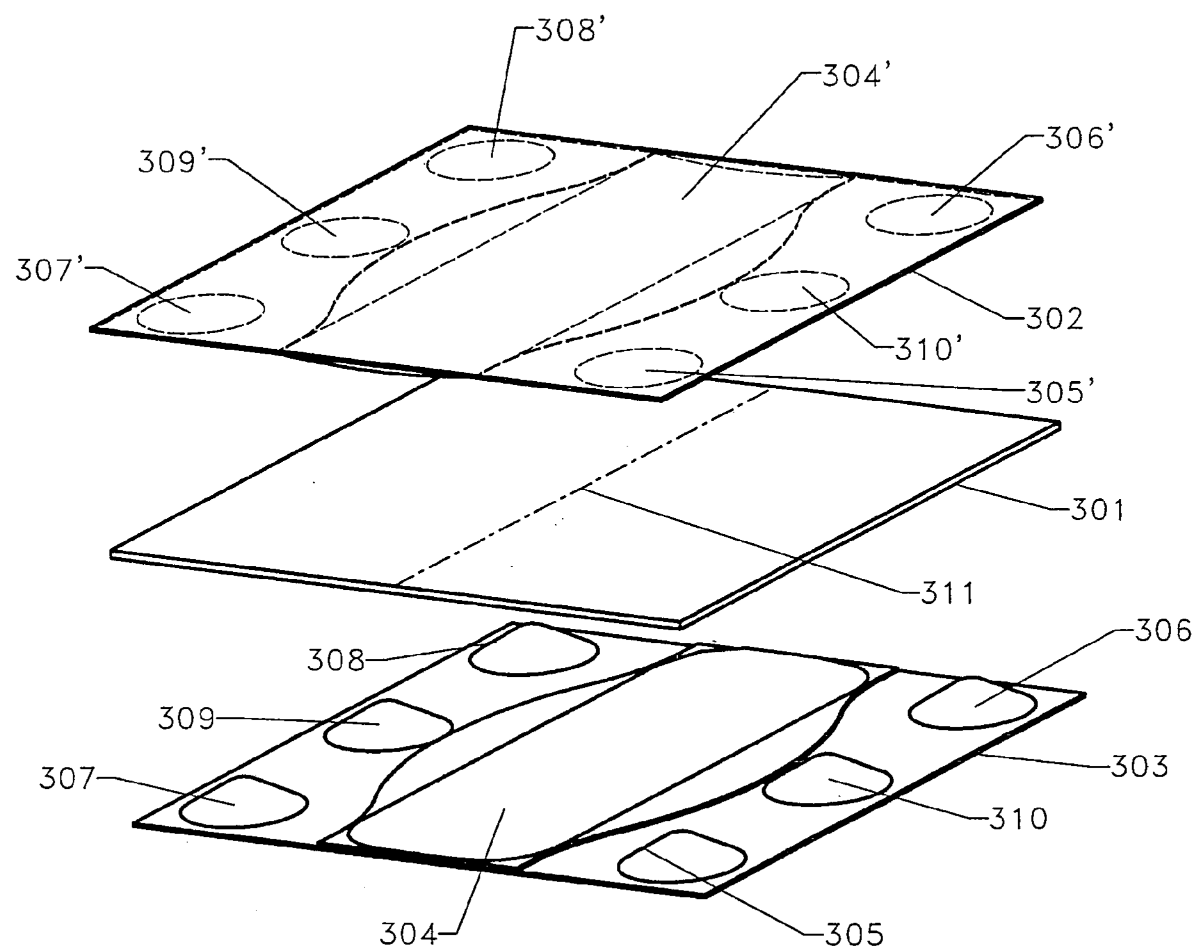
FIG. 3 is an exploded view of a grid holding device according to an embodiment of the invention.

FIG. 1 schematically shows an X-ray system according to prior-art technique. Secondary X-ray radiation grids, hereinafter referred to as X-ray grids, are used in X-ray systems to obtain a more distinct image of an irradiated object.

Usually an X-ray system is composed as schematically shown in cross-section in FIG. 1. A radiation source 101 emits X-ray radiation 102, which passes through an examined object 103, such as a human body, and reaches an X-ray film 104, which is exposed to the radiation. The intensity of the radiation which reaches the X-ray film 104 varies over the surface of the film depending on the characteristics of the inner structures of the object 103. If the object 103 is a human body, an image of the skeleton in the body can thus be recorded.

The X-ray radiation 102 emitted by the radiation source 101 may be referred to as primary radiation. Such primary radiation can generate secondary radiation. This may occur if primary radiation excites an atom, for example, in a skeleton tissue in the object 103. This atom can then emit secondary radiation 105 in a random direction. If the secondary radiation reaches the X-ray film 104 noise occurs in the image, i.e. the image will be less clear.

In order to shield the X-ray film 104 from such secondary radiation, an X-ray grid 106 is used, which is located in the vicinity of the film. The X-ray grid 106 is composed of a number of slats 107 of lead, which are spaced apart with the aid of spacers 108, which contrary to the slats 107 are made of a material which does not absorb X-rays. The grid thus resembles a stack of narrow strips of lead with spacers made of a material which does not absorb X-rays. In its assembled state, the X-ray grid 106 is composed of a plate with dimensions of, for example, 40×40 cm and a thickness of, for example, 2 mm. The cross-sectional long sides of the slats 107, which in FIG. 1 are also shown on a larger scale in cross-section perpendicular to their longitudinal direction, are oriented such that primary radiation 102, emitted directly from the radiation source 101, will propagate parallel with the planes of the slats 107. The secondary radiation 105, however, will be absorbed by the surfaces of the slats, except for the small portion of the secondary radiation 105 that is parallel with the primary radiation 102 in the plane of the cross-section. It is to be noted that also a small portion of the primary radiation 102 is absorbed by the X-ray grid, since the slats 107 have a certain thickness. To enable the system described above to function satisfactorily, the radiation source 101 has to be placed at a distance from the grid 106 that substantially corresponds to the convergence distance there of, i.e. at the distance from the grid (and on the correct side of the grid) where the planes of the slats coincide in a line.

FIG. 2 is a cross-sectional view schematically showing the function of a grid device according to an embodiment of the invention. In this case, the grid can be flexed in two directions.

When the grid is flat, as shown at 201, it has a first convergence distance 202, for example 120 cm. This corresponds to a first optimum positioning 203 of a radiation source.

The grid holding device which supports the grid comprises flexing means, which will be described below, for flexing the grid in a first direction to a first predetermined flexed position, indicated by dashed lines at 204. In this position, the grid more or less approximately describes part of the circumferential surface of a circular cylinder having its centre line to the right of the grid in FIG. 2. In the position 204, the grid has a second convergence distance 205 (longer than the first one), for example 180 cm. At 206, a corresponding optimum positioning of a radiation source is shown. In this position, the slats of the grid are more parallel than in the flat initial position.

The grid holding device also comprises flexing means for flexing the grid in a second direction opposite to the first direction to a second flexed position, indicated by dot-dashed lines at 207. In this position, the grid more or less approximately describes part of the circumferential surface of a circular cylinder having its centre line to the left of the grid in FIG. 2. In the position 207, the grid has a third convergence distance 209 (shorter than the first one), for example 80 cm. In this position, the slats of the grid are less parallel than in the initial position.

At 209, a corresponding optimum positioning of a radiation source is shown.

FIG. 3 is an exploded view of a grid holding device according to an embodiment of the invention. The device cooperates with a grid 301 accommodated in the grid holding device, which is in the form of a box with an X-ray transparent lid 302 and an X-ray transparent bottom 303. The walls of the box interconnecting the lid and the bottom are not shown. When used in an X-ray system, the box is placed between the object that is to be irradiated and the X-ray plate/film that is to be exposed.

At the bottom 303 of the box, a first inflatable element 304 is placed, which in the inflated state exerts a load on the X-ray grid so as to flex the same in said first direction. The element 304 is arranged about a centre line 311 of the grid 301. A corresponding element 304', which is indicated by dashed lines in FIG. 3, is arranged at the underside of the lid 302. This element 304' serves to flex the grid in a second opposite direction.

Six beads 305–310 are arranged at the bottom 303 of the box. Corresponding beads 305'–310', which are indicated by dashed lines, are arranged at the underside of the lid 302. Each one of the beads 305–310 at the bottom of the box forms, together with the corresponding beads 305'–310' at the underside of the lid, a pair of beads which serves to fix the grid 301 in the box. The beads are arranged to secure the grid 301 at the edges on both sides of the centre line 311. In this case, the beads are placed in the corners of the grid 301 and halfway between the corners at said edges, but it is also conceivable, for example, to combine the beads 305, 310 and 306 into one elongate bead extending along the entire edge. As an alternative to the beads, it is possible to use folds in the grid box, but in that case the grid 301 should be substantially centred between the lid 302 and the bottom 303 in its flat state. Furthermore, the grid should be pushed into the box in the longitudinal direction of the folds.

Figure 4A:
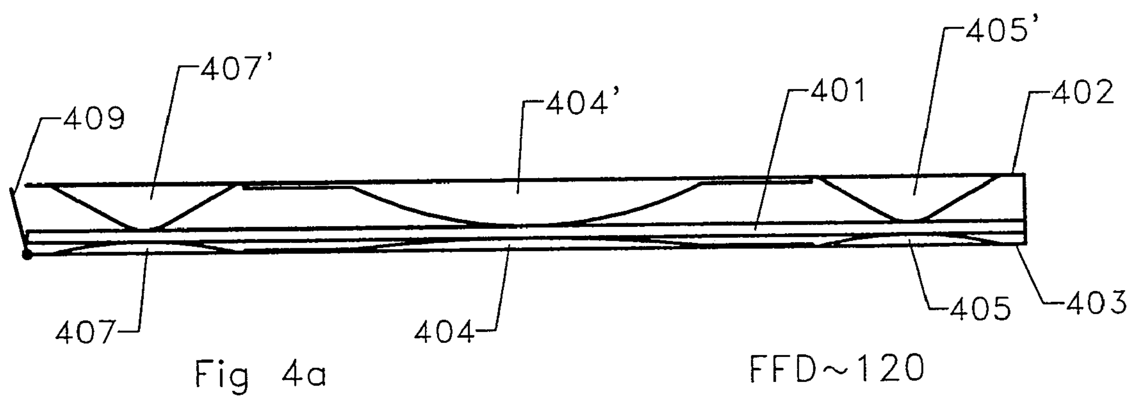
FIG. 4*a* schematically shows a grid holding device according to FIG. 3 in which the grid holding device is in a first position/state.

FIG. 4*a* schematically shows a grid holding device corresponding to that shown in FIG. 3, which grid holding device is in a first position. In FIG. 4*a*, the device in FIG. 3 is seen along the centre line 311, from the edge of the device where the beads 305 and 307 are located, the wall interconnecting the lid and the bottom being removed. As already mentioned, the grid holding device comprises a lid 402 and a bottom 403. The grid 401 can be inserted and removed (pushed in or out) through an openable door 409 in the box. FIG. 4*a* shows how the beads 405 and 407 (corresponding to 305 and 307 in FIG. 3) cooperate with the other beads in the respective pairs 405' and 407' to resiliently hold and fix the grid 401 in the box. For this purpose, the beads are made of an elastic material. They can be filled with air or, for example, a foamed plastic material. In FIG. 4*a*, the upper beads 405', 407' in each pair are inflated, whereas the lower beads (405, 407) are more or less evacuated. In the shown example, the grid 401 is thus located in the vicinity of the bottom 403 of the box. It is also conceivable to centre the grid 401 in its flat position in a position halfway between the lid 402 and the bottom 403. In that case, the beads in each pair (for example 407, 407') can have the same size, which makes it unnecessary to vary their size. The beads can then also be solid. The arrangement shown in FIG. 4*a* also gives the advantage that the bottom 403 prevents undesirable downward flexing of the grid 401 due to its own weight in the shown horizontal position. In FIG. 4*a*, the inflatable elements 404, 404' are also shown.

In the flat state, the grid has a convergence distance (FFD) of 120 cm.

Figure 4B:
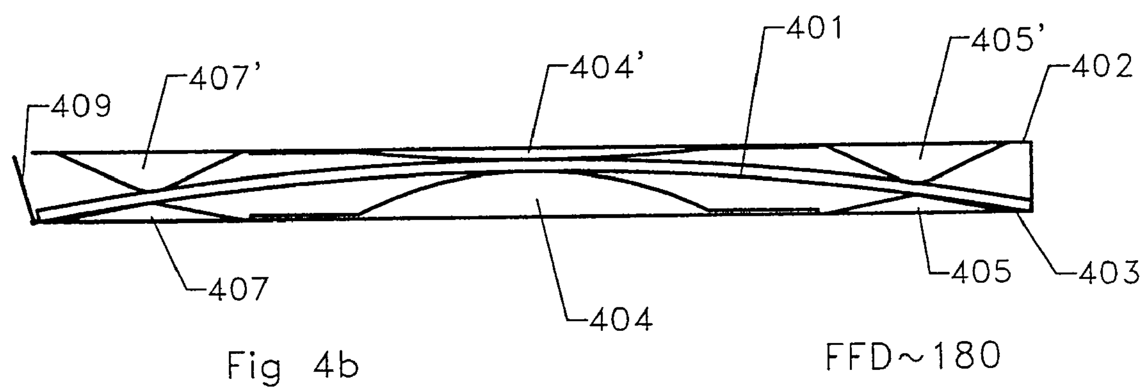
FIG. 4*b* shows the grid holding device in FIG. 4*a* in a second position.

In FIG. 4*b*, the grid holding device in FIG. 4*a* is shown in a second position. The inflatable element 404 (corresponding to 304 in FIG. 3) is here shown in an inflated state. This element 404 can be made as a tight bag or balloon fixed to the bottom 403 of the box. Alternatively, it can be a membrane, whose edges are welded to the bottom 403 of the box, so that an air-tight space is formed. The element 404 comprises an elastic wall, which when the element is inflated is pressed against the grid 401 and flexes it. The element 404 is inflated, for example with air, through a hose (not shown). The upper beads 405', 407' are kept inflated. The grid 401 is thus flexed so that the centre line of the grid 401 is moved upwards in the Figure and the edges on both sides of the centre line are moved downwards. This is achieved by means of the inflatable element 404 and the beads 405', 407', and the grid 401 then has a convergence distance of 180 cm.

The underside of the lid 402 of the box can optionally be provided with an abutment (not shown) in the form of a part of the circumferential surface of a circular cylinder. When the element 404 is heavily inflated, the grid is pressed against the abutment, thereby assuming a desirable shape.

The extension of the inflatable element 404 in the plane of the bottom 403 can be adjusted to the bending stiffness of the grid 401 to provide a suitable effect over the width of the grid, thereby giving the grid an optimally flexed form. Another possibility is to arrange a plurality of inflatable elements which in the inflated state press against one surface of the grid 401 and preferably in the area round the centre line 311 shown in FIG. 3. The pressure in these elements can optionally be varied individually.

Figure 4C:
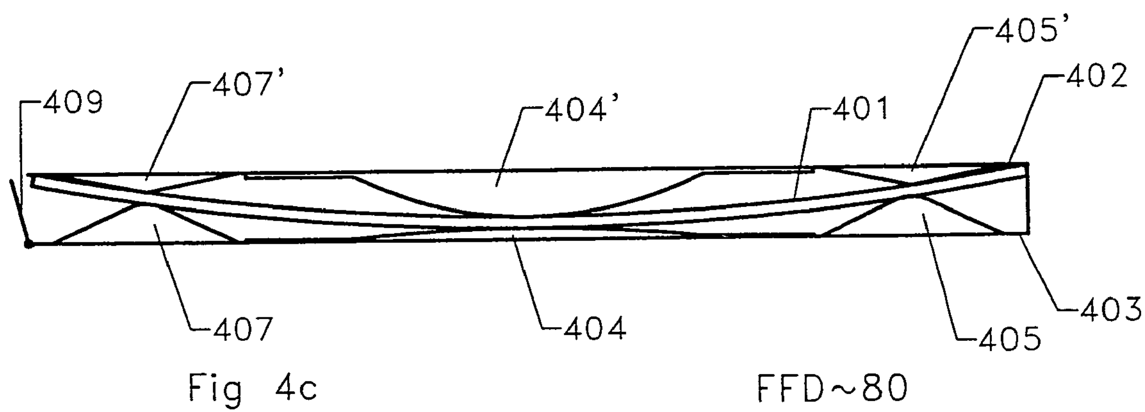
FIG. 4*c* shows the grid holding device in FIG. 4*a* in a third position.

In FIG. 4*c*, the grid holding device in FIG. 4*a* is shown in a third position. The inflatable element 404' is now used like the element 404 in FIG. 4*b*. The element 404 which is inflated in FIG. 4*b* is here substantially void of air and does not affect the grid 401. At the same time, the lower beads (for example 405, 407) in each pair are inflated, so that the opposite edges of the grid on both sides of the centre line are moved towards the lid 402 of the box. The upper beads 405', 407' are substantially evacuated. This results in the grid 401 being flexed in a direction opposite to that in FIG. 4*b*. The convergence distance is now 80 cm.

Summing up, the invention relates to a grid holder for an X-ray diagnostic system. The grid holder cooperates with a flexible X-ray grid, which in a flat state has a first focus distance/convergence distance of about 120 cm. A flexing means, preferably in the form of an inflatable element, which can exert a pressure on the surface of the grid, is arranged to flex the grid in a first direction to a first position in which it has a second convergence distance of about 180 cm. Another corresponding flexing means is arranged to flex the grid in the opposite direction to a second position in which it has a third convergence distance of about 80 cm. This allows variable convergence distances with minimum flexing of the grid. The invention also relates to grid devices with grid holders and grids as well as X-ray diagnostic systems comprising such grid holders/grid devices.

The invention is not limited to the embodiments described above, but can be varied within the scope of the appended claims.

The invention claimed is:

1. A grid holding device for a medical X-ray diagnostic system, which device is adapted to cooperate with a flexible, plate-shaped X-ray grid (401), which in a flat state has a first convergence distance, and which device comprises a flexing means for flexing the X-ray grid in order to adjust the convergence distance of the X-ray grid, wherein the flexing means comprises a first means (404) for flexing the X-ray grid in a first direction from the flat state to a first predetermined flexed position, in which the grid has a second convergence distance, which is longer than the first convergence distance, and a second means (404') for flexing the X-ray grid in a second direction from the flat state to a second predetermined flexed position, in which the grid has a third convergence distance, which is shorter than the first convergence distance.

2. A grid holding device as claimed in claim 1, in which the first means for flexing comprises a first inflatable element (404) with an elastic wall, which is arranged to exert a pressure, when the element is inflated, on one surface of the X-ray grid (401).

3. A grid holding device as claimed in claim 2, in which the second means for flexing comprises a second inflatable element (404') with an elastic wall, which is arranged to exert a pressure, when the second element is inflated, on the other surface of the X-ray grid (401).

4. A grid holding device as claimed in claim 3, in which the walls of the inflatable elements are arranged to exert a pressure on the X-ray grid in an area, which is located about a centre line (311) between two opposite edges of the grid (301).

5. A grid holding device as claimed in claim 1, further comprising a box with a lid (402) and a bottom (403), which box is arranged to contain the X-ray grid (401) and in which box said first (404) and second (404') means for flexing are accommodated.

6. A grid holding device as claimed in claim 5, in which the box comprises at least a first (405, 405') and a second (407, 407') pair of resilient beads, the first bead (405, 407) in each pair being attached to the underside of the lid (402) and the second bead (405', 407') in each pair being attached to the bottom (403) of the box, opposite the first bead in the respective pairs, and the pairs of beads being arranged to fix the X-ray grid (401) in the box.

7. A grid holding device as claimed in claim 6, in which the pressure in at least one of the beads is variable.

8. A grid device, comprising a flexible, plate-shaped X-ray grid (401), which in a flat state has a first convergence distance, and a grid holding device as claimed in claim 1.

9. A grid device as claimed in claim 8, in which the first convergence distance is in the range of 110–130 cm, the second convergence distance is in the range of 170–190 cm and the third convergence distance is in the range of 70–90 cm.

10. An X-ray diagnostic system, comprising a grid holding device as claimed in claim 1.

11. An X-ray diagnostic system, comprising a grid device as claimed in claim 8.

12. A grid holding device as claimed in claim 2, further comprising a box with a lid (402) and a bottom (403), which box is arranged to contain the X-ray grid (401) and in which box said first (404) and second (404') means for flexing are accommodated.

13. A grid holding device as claimed in claim 3, further comprising a box with a lid (402) and a bottom (403), which box is arranged to contain the X-ray grid (401) and in which box said first (404) and second (404') means for flexing are accommodated.

14. A grid holding device as claimed in claim 4, further comprising a box with a lid (402) and a bottom (403), which box is arranged to contain the X-ray grid (401) and in which box said first (404) and second (404') means for flexing are accommodated.

15. A grid device, comprising a flexible, plate-shaped X-ray grid (401), which in a flat state has a first convergence distance, and a grid holding device as claimed in claim 2.

16. A grid device, comprising a flexible, plate-shaped X-ray grid (401), which in a flat state has a first convergence distance, and a grid holding device as claimed in claim 3.

17. A grid device, comprising a flexible, plate-shaped X-ray grid (401), which in a flat state has a first convergence distance, and a grid holding device as claimed in claim 4.

18. An X-ray diagnostic system, comprising a grid holding device as claimed in claim 2.

19. An X-ray diagnostic system, comprising a grid holding device as claimed in claim 3.

20. An X-ray diagnostic system, comprising a grid device as claimed in claim 9.

* * * * *